(12) United States Patent
Shahriar

(10) Patent No.: US 12,090,363 B2
(45) Date of Patent: Sep. 17, 2024

(54) BILATERAL LEFT AND RIGHT BRAIN COORDINATION ACTIVITY SYSTEM

(71) Applicant: Khaled Shahriar, New Hyde Park, NY (US)

(72) Inventor: Khaled Shahriar, New Hyde Park, NY (US)

(*) Notice: Subject to any disclaimer, the term of this patent is extended or adjusted under 35 U.S.C. 154(b) by 235 days.

(21) Appl. No.: 15/936,408

(22) Filed: Mar. 26, 2018

(65) Prior Publication Data

US 2019/0290958 A1   Sep. 26, 2019

(51) Int. Cl.
| | | |
|---|---|---|
| A63B 23/00 | (2006.01) | |
| A63B 21/00 | (2006.01) | |
| A63B 23/035 | (2006.01) | |
| A63B 23/12 | (2006.01) | |
| A61B 5/11 | (2006.01) | |
| A63B 22/00 | (2006.01) | |
| A63B 71/06 | (2006.01) | |
| G09B 19/00 | (2006.01) | |

(52) U.S. Cl.
CPC .... *A63B 23/03516* (2013.01); *A63B 21/4033* (2015.10); *A63B 23/12* (2013.01); *A61B 5/1124* (2013.01); *A63B 2022/0092* (2013.01); *A63B 2071/0652* (2013.01); *G09B 19/003* (2013.01)

(58) Field of Classification Search
CPC .................................................. A63B 23/03516
USPC ...................................................... 434/258
See application file for complete search history.

(56) References Cited

U.S. PATENT DOCUMENTS

| | | |
|---|---|---|
| 3,721,440 A | 3/1973 | Burns |
| 3,784,194 A | 1/1974 | Perrine |
| 4,082,267 A | 4/1978 | Flavell |
| 4,268,254 A | 5/1981 | McCormick |
| RE40,427 E | 7/2008 | Nashner |
| 8,512,043 B2 | 8/2013 | Choquet |
| 8,915,739 B2 | 12/2014 | Schulken |
| 9,623,307 B1 | 4/2017 | Devor |
| 9,827,462 B2 | 11/2017 | Siqueira |

(Continued)

FOREIGN PATENT DOCUMENTS

| | | |
|---|---|---|
| CN | 201035774 Y | 3/2008 |
| EP | 0944176 A1 | 9/1999 |

(Continued)

*Primary Examiner* — Kesha Frisby
(74) *Attorney, Agent, or Firm* — Yong Chen

(57) ABSTRACT

The current invention is a Bilateral Brain Coordination Activity System requiring simultaneous performance of a set of tasks assigned to two or more extremities, e.g. hand, finger and foot. The purpose of this invention is to enhance coordination between left and right brain. The set of tasks consist of symmetric or asymmetric differentiated motions, wherein each motion requiring a distinct brain command, and therefore bilateral brain coordination. The system employs a mechanical and/or interactive digital platform with handheld or stationary devices, or rideable equipment. Difficulty level varies with the selected set of tasks, their spatial and planar arrangement and the number of involved extremities. This invention is appropriate for all ages to improve bilateral coordination and motor skill, and can be for individual use, sportsman and military training, identification of motor skill deficits, therapeutic development of compromised motor skill, and/or entertainment or game use.

9 Claims, 7 Drawing Sheets

Mechanical activity unit with interchangeable modular tasks (middle image)

(56) References Cited

U.S. PATENT DOCUMENTS

| | | |
|---|---|---|
| 2003/0118975 A1 | 6/2003 | Stamm et al. |
| 2003/0207739 A1 | 11/2003 | Whitall et al. |
| 2006/0094573 A1 | 5/2006 | Weck |
| 2006/0293617 A1* | 12/2006 | Einav .................... G06F 3/016 601/33 |
| 2008/0132383 A1 | 6/2008 | Einav et al. |
| 2009/0068621 A1 | 3/2009 | Schulken |
| 2009/0305207 A1 | 12/2009 | Ueshima et al. |
| 2010/0068686 A1 | 3/2010 | Ueshima |
| 2011/0112441 A1 | 5/2011 | Burdea |
| 2014/0371633 A1 | 12/2014 | Evin et al. |
| 2015/0065009 A1* | 3/2015 | Chase ...................... A63H 3/52 446/444 |
| 2015/0125838 A1 | 5/2015 | Pack |
| 2016/0144229 A1 | 5/2016 | Aluru et al. |

FOREIGN PATENT DOCUMENTS

| | | | |
|---|---|---|---|
| KR | 20090072082 A | 7/2009 | |
| KR | 101608118 B1 | 4/2016 | |
| WO | WO-2011138623 A1 * | 11/2011 | ........... A63F 9/0078 |

\* cited by examiner

Fig. 1a –1c: Illustration of Activity Unit Types
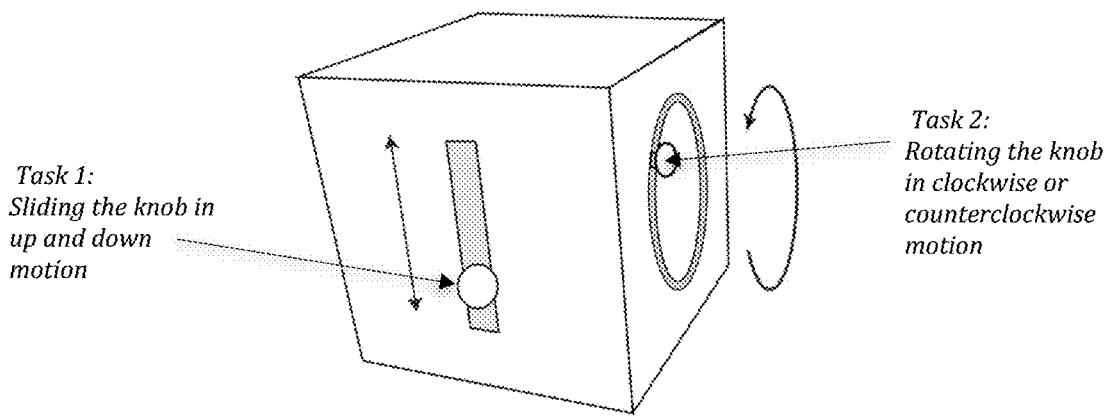
Fig. 1a- Mechanical activity unit with pre-assigned tasks (top image)
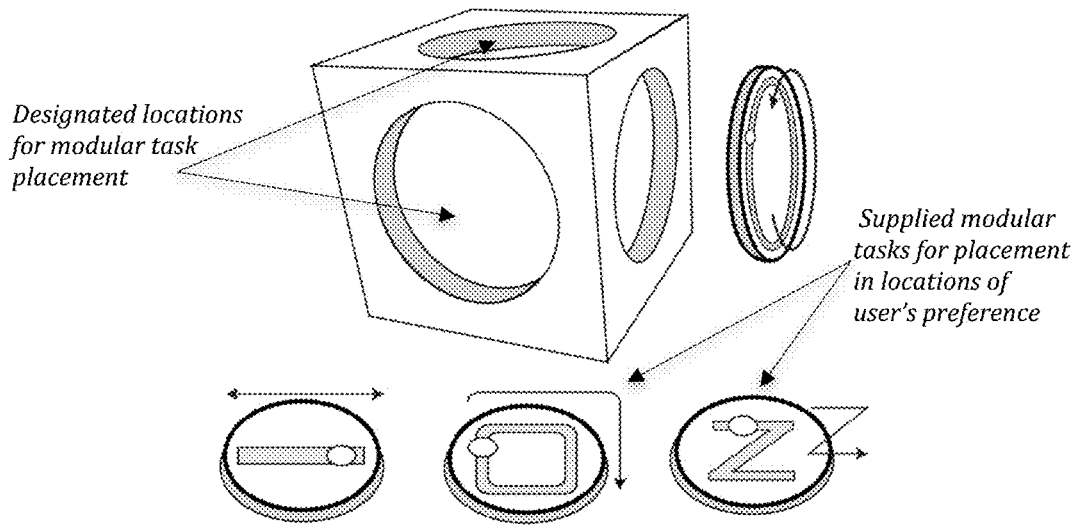
Fig. 1b- Mechanical activity unit with interchangeable modular tasks (middle image)
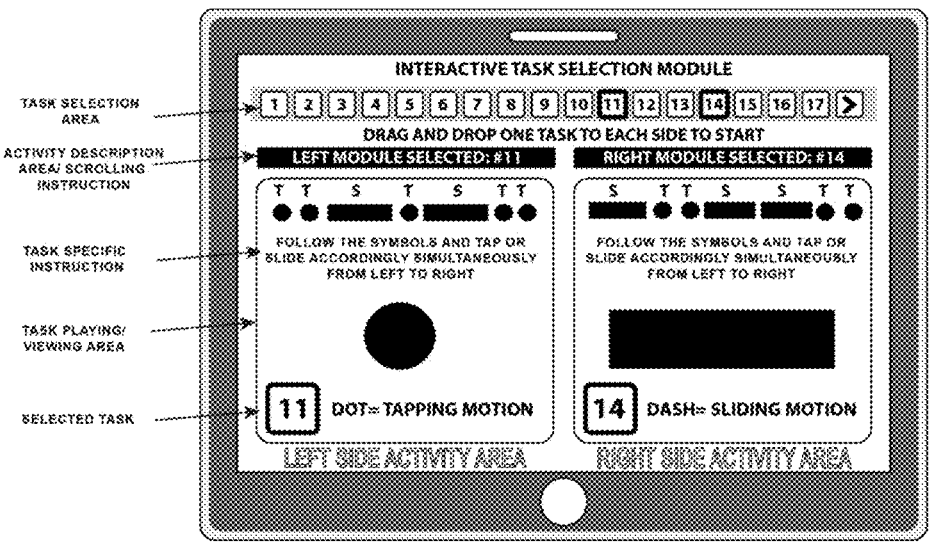
Fig. 1C- Interactive digital activity unit with selectable tasks (bottom image)

Fig. 2a- 2j: Illustration of Differentiated Motions (Rows are Symmetric, Columns are Asymmetric, with motions consisting of Straight, Curved, or Irregular Paths)

*Fig. 2a*
*Sliding left and right motion*

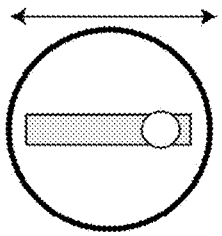

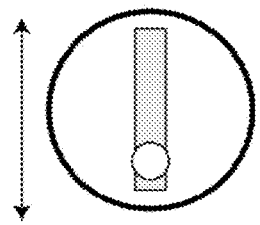

*Fig. 2b*
*Sliding up and down motion*

*Fig. 2c*
*Counterclockwise rotational motion*

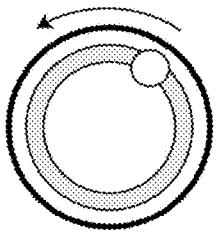

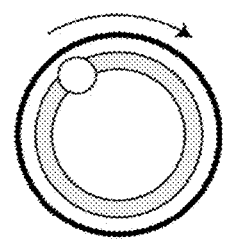

*Fig. 2d*
*Clockwise rotational motion*

*Fig. 2e*
*Clockwise rectangular path motion*

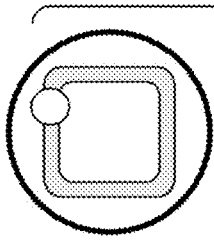

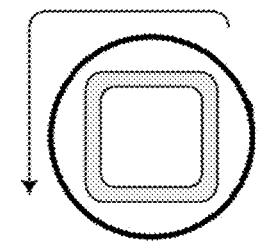

*Fig. 2f*
*Counterclockwise rectangular path motion*

*Fig. 2g*
*Irregular linear motion (forward Z path)*

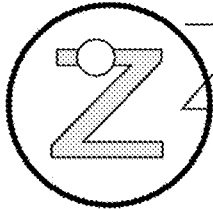

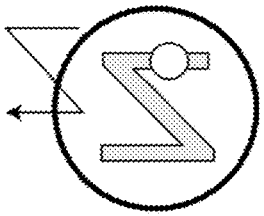

*Fig. 2h*
*Irregular linear motion (reverse Z path)*

*Fig. 2i*
*Irregular curved motion (forward 6 path)*

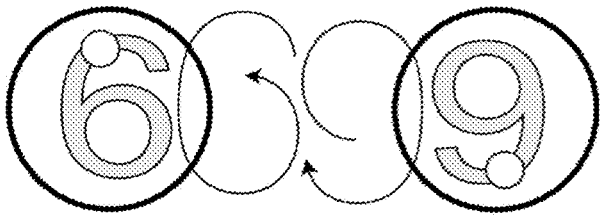

*Fig. 2j*
*Irregular curved motion (forward 9 path/ inverted 6 path)*

Fig. 3a –3c: Illustration of Planar Orientation.
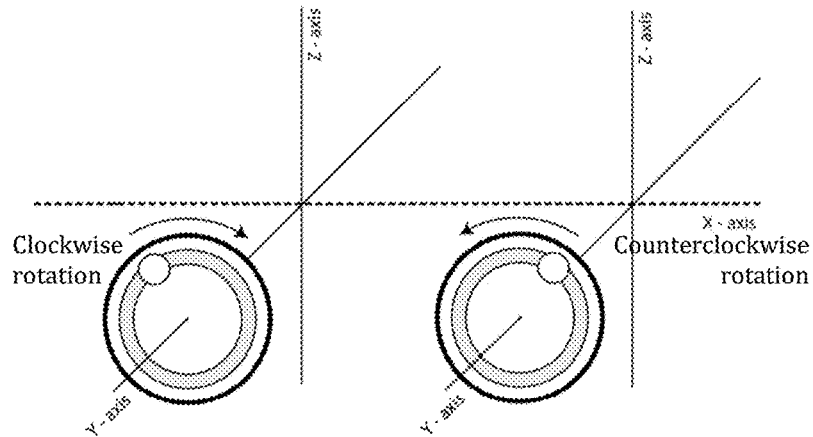
*Fig. 3a-* Single Plane Orientation (top image)
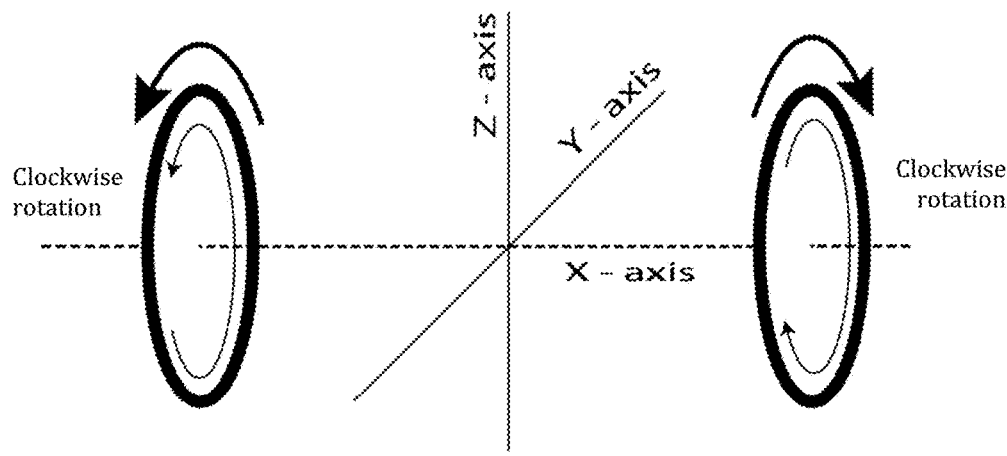
*Fig. 3b-* Out-facing Planar Orientation of Activity (middle image)
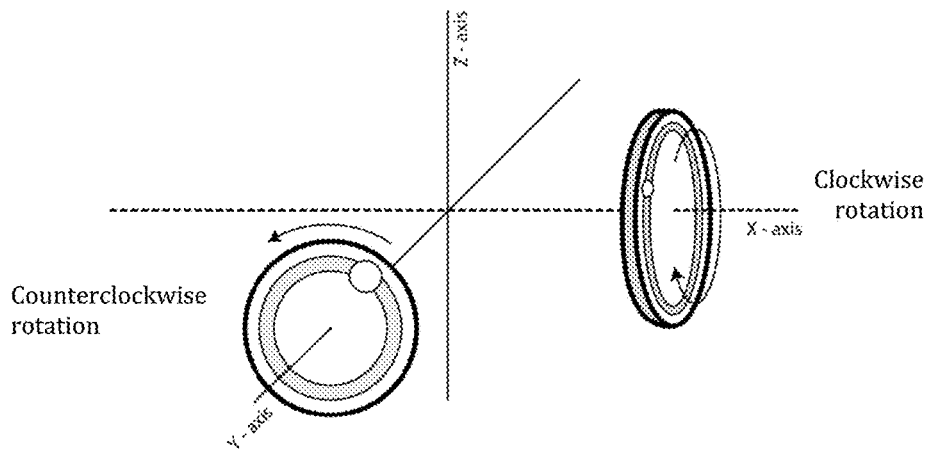
*Fig. 3c-* Perpendicular Planar Orientation (bottom image)

Fig. 4a – 4f: Illustration of Shape Configurations of mechanical activity units
*Note: CW = Clockwise, CCW = Counterclockwise*
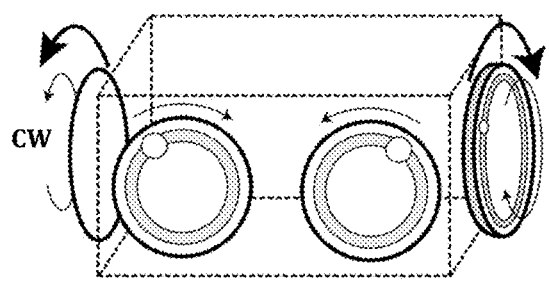
*Fig. 4a*- Rectangular Solid
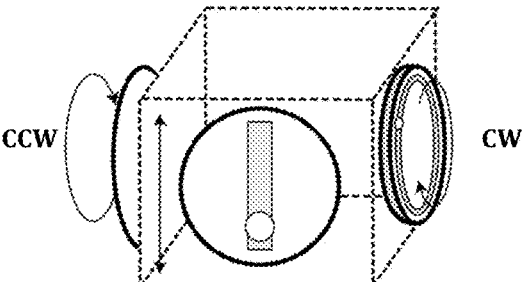
*Fig. 4b*- Cube
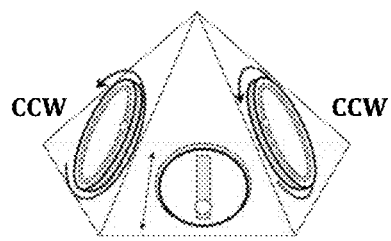
*Fig. 4c*- Pyramid
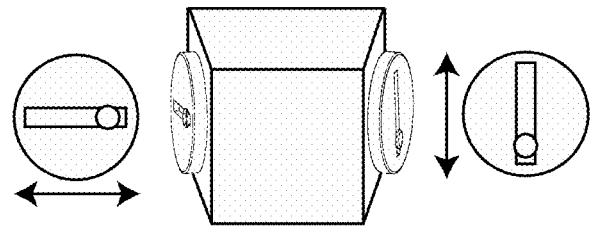
*Fig. 4d*- Oblique Rectangular solid
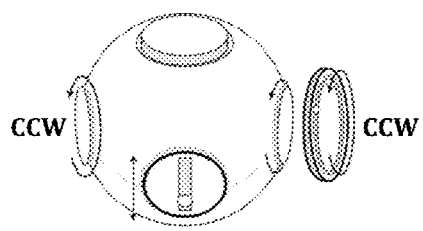
*Fig. 4e*- Sphere
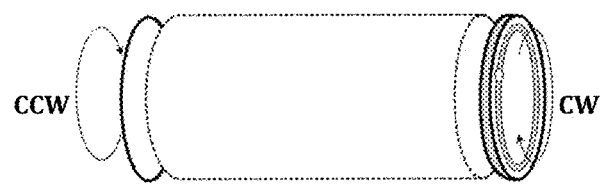
*Fig. 4f*- Cylinder Fig. 5a-5b: Illustration of Interactive activity unit utilizing motion sensor handheld input.
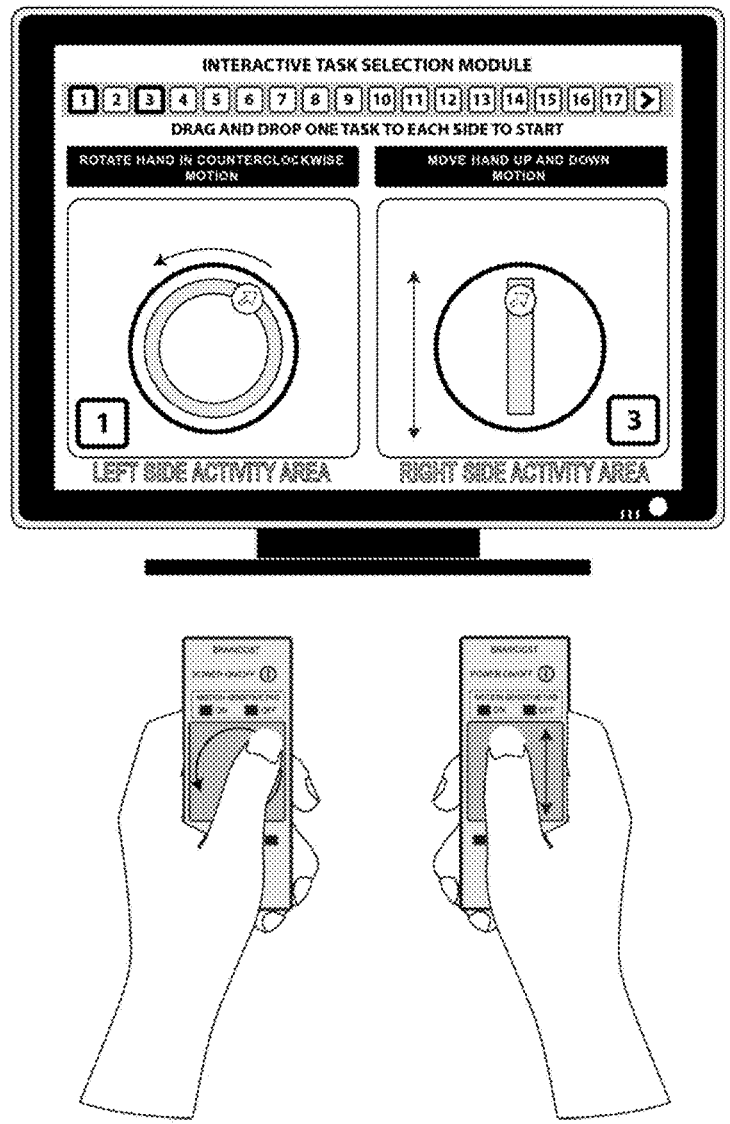
*Fig. 5a-* Using Handheld touch-sensitive remote control to perform selected tasks
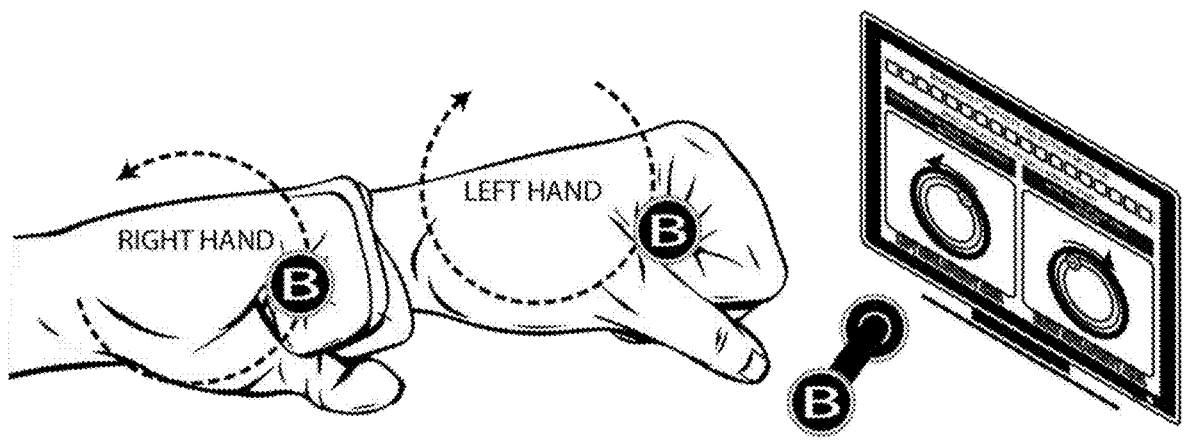
*Fig. 5b-* Using Handheld motion sensor dumbbells to perform selected task Fig. 6a-6c: Illustration of Extremity Involvement
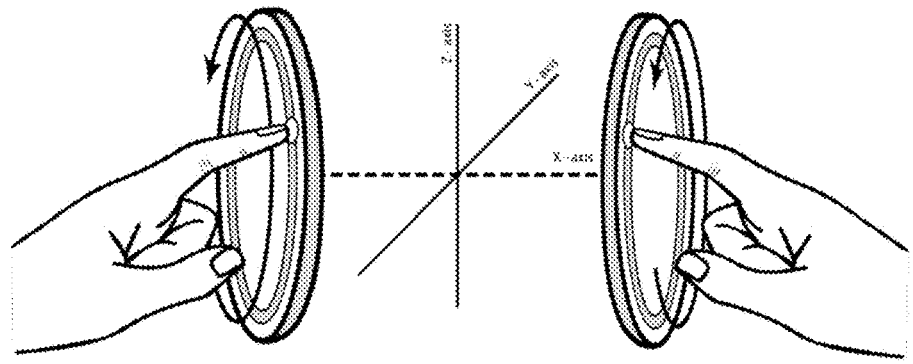
Fig. 6a- Two fingers involved on mechanical activity unit.
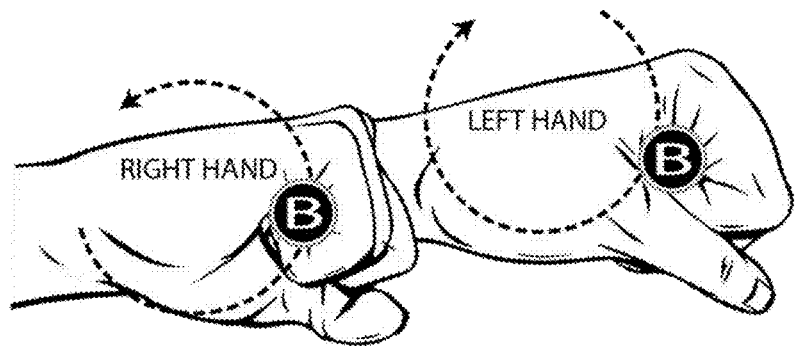
Fig. 6b- Two hands involvement on interactive activity unit.
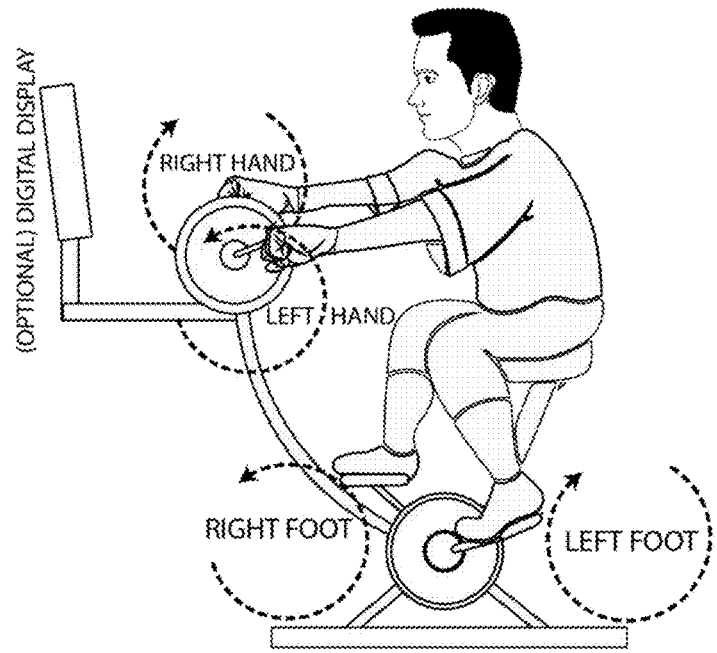
Fig. 6c- Four extremities involvement on Rideable unit.

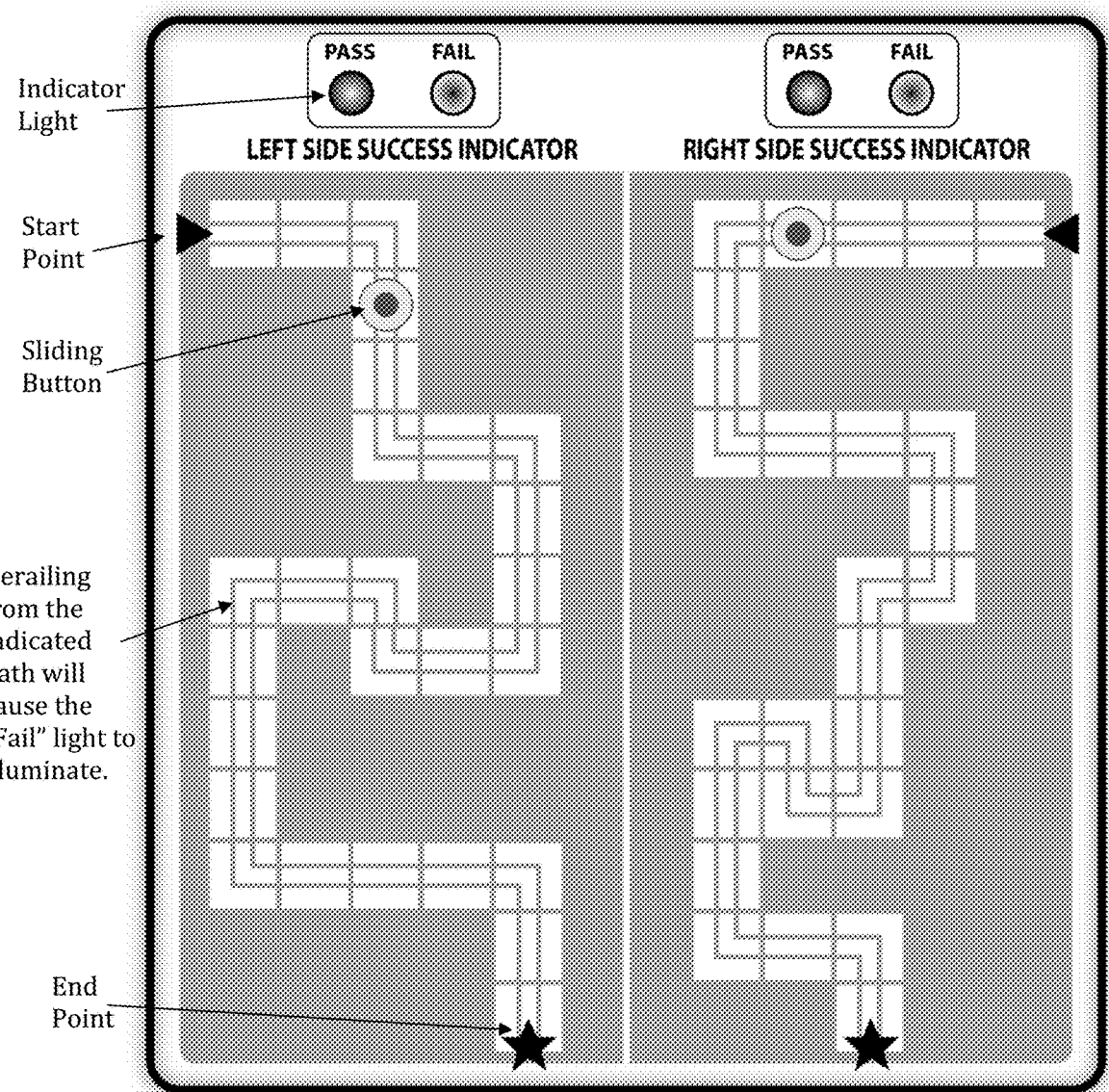
Fig. 7- Illustration of mechanical activity unit utilizing electronic feedback.

BILATERAL LEFT AND RIGHT BRAIN COORDINATION ACTIVITY SYSTEM

BACKGROUND OF THE INVENTION

The human brain is the most powerful computer. It controls reasoning and decision-making, interprets sensory stimuli and directs every motion and motor activity. It gives us the ability to think and react logically when using motor activities to perform a given task. The brain consists of left and right hemispheres.

According to Roger W. Sperry, psycho-biologist and Nobel Prize winner in 1981, the left side of the brain is more verbal, analytical and is associated with logic, sequencing, linear thinking, mathematics, facts, thinking in words. The right side of the brain is more visual and intuitive and is associated with imagination, holistic thinking, intuition, arts, rhythm, nonverbal cues, feelings, visualization, daydreaming.

The motor areas of each brain hemisphere direct muscles on the opposite side of the body, therefore activities performed by left side of the body are controlled by the right hemisphere and vice versa. For motor activities requiring both sides of the body, both hemispheres of the brain must coordinate to perform, also known as bilateral coordination.

Immediately after birth, babies start reacting to external stimuli, and gradually learn to visually follow moving objects and sounds, to grasp objects, to roll over and to sit. Eventually a child learns to move objects, stand up, walk and run. These stages are inherent to development. All motor activities require use of body organs and/or extremities, and are all controlled by the brain's ability to direct and coordinate left and right brain hemispheres.

Performance of any task by an extremity requires a command from the brain. Therefore, multiple commands are necessary when multiple tasks are required to be performed by our extremities. Bilateral brain coordination becomes more significant when multiple extremities are involved in complex motions that are more opposing or asymmetric than symmetric or alternating motions. Simple examples of symmetric alternating motions using multiple extremities are the act of walking, swimming, cycling etc. The ability to perform these motions is not hereditary, it is learned. An example of a complex set of motions is for a person to simultaneously move left hand and right foot in alternating upward-downward motion while their right hand and left foot to describe a circular motion.

People exhibit diverse ability levels in performance of motor functions, and the skill levels they are able to achieve are often dictated by their passion, profession, practice and desire for perfection. Most complex motor functions require complex brain coordination, and individual performance in use of their extremities varies. A sportsman or athlete may exhibit performance of complex motor functions through bilateral coordination differently than a classical dancer or a musician. Practicing these complex motions generally results in significant improvement of the level of bilateral coordination in perfecting these skill sets. The skills of typing on a keyboard, playing a piano, using a hand tool, climbing a mountain are all examples of activities requiring finite bilateral brain coordination, and all are improved, if not perfected, with practice. Similarly, practice of certain assistive tasks usually develops the ability to perform motor activities for those who are physically and/or developmentally challenged.

Daily activities include countless tasks, each consisting of singular or multiple motions, some simple and others complex. Individual bilateral coordination capabilities vary in performance of complex activities, but they can be enhanced. This invention provides a system of activity units or exercising devices ranging from simpler to challenging motor activities designed to stimulate brain coordination through engaging multiple extremities to perform set of tasks of varied levels of complexity, and hence improve bilateral coordination ability. This system of activity units can be utilized for entertainment, therapeutic value, or training, and it is the inventor's belief that users will experience enhancement of bilateral coordination skills.

DESCRIPTION OF DRAWINGS

FIG. 1a: Illustrates an example of a mechanical activity unit with pre-assigned tasks; commercial units will vary in the scope of color, size, shape, availability of tasks. The installed tasks will be permanently installed in various combinations of motions. On the unit shown, the user is required to perform a linear sliding up and down motion with one hand and a circular rotating motion with the other.

FIG. 1b: Illustrates a mechanical activity unit with a representative sample of interchangeable modular tasks and designated receptacles for their placement on each face; commercial units will be fabricated in various colors, sizes and shapes. Modular tasks are provided separately in paired sets consisting of matched sizes, shapes and difficulty levels. In this illustration, the cube has designated receptacles on each face, and modular tasks are supplied to attach in these positions. A representative sample of shapes is shown. Modular tasks are available to suit user-desired skill levels.

FIG. 1c: Illustrates an interactive digital activity unit utilizing touchscreen devices. Other illustration of interactive activity units utilizing Bluetooth technology motion sensitive devices are shown on FIG. 5a, 5b. The digital application displays the activity areas wherein the tasks are required to be performed.

In this illustration, the number 11 task has been chosen for the left side activity area from the task selection menu on the top of the screen, and number 15 has been chosen for the right side, for the demonstration purposes. These chosen tasks are sequences of tapping and sliding motions with fingers as indicated at the top of the activity area. The user is required to simultaneously tap or slide a fingertip of each hand to perform the sequence displayed for each activity area. As the user executes the displayed action, the next required action is displayed until all required actions are completed. For the sample task sequence shown, the user will tap, tap, slide, tap, slide, tap, tap with the left hand, and simultaneously will slide, tap, tap, slide, slide, tap, tap with right hand.

FIG. 2a-2j: Illustrations of several examples of differential motions that follow various paths. These differential motions are available as options of tasks to choose from for mechanical units as pre-assigned as shown in FIG. 1a, or interchangeable modular tasks and for interactive applications as shown in FIG. 1b or FIG. 4a-4f.

In this illustration, motions are symmetric by row, and asymmetric by column. Types of motions must be defined with regards to this drawing and row/column association for an understanding of the application of the activities available in this invention as illustrated. In all occurrences where direction of movement is specified e.g. left, right, up, down, in, out, clockwise or counterclockwise, all are from a point of view perpendicular to the direction of movement.

Symmetric motions are identical paths of two or more motions. When performed on a single plane e.g. FIG. 2d in which both tasks are performed in clockwise circular motion with both hands, the brain commands are symmetric and identical. However, if one hand moves in counterclockwise circular motion e.g. FIG. 2c and the other hand follows clockwise circular motion on a single plane e.g. FIG. 2d, then although the motions are symmetric, this requires both side of the brain to perform two distinct commands requiring bilaterally coordination to perform the activity. These are opposing symmetric motions.

Asymmetric motions are distinct paths of two or more motions bearing no resemblance e.g. motion shown on FIG. 2a is different from that of FIGS. 2c, 2e, 2g and 2i. When performed simultaneously, the asymmetric motions also require both sides of the brain to perform two distinct commands that are required to be bilaterally coordinated to perform the activity.

FIG. 3a: Illustration of a single plane orientation of tasks that are performed side-by-side on a single plane. This arrangement generally provides the easiest level of difficulty for most symmetric motions. Asymmetric tasks using this configuration will impose higher levels of difficulty. On the shown illustration, the right extremity is required to describe a circle in counterclockwise motion and the left side to perform a clockwise motion.

FIG. 3b: Illustration of tasks arranged in parallel planes facing away from each other on the same axis. In this arrangement, difficulty levels increase for symmetric motions or asymmetric motions with opposing direction of motion. On the shown illustration, the directions of motions are both clockwise, however they are in opposing direction to each other. These motions are of moderate difficulty.

FIG. 3c: Illustration of activity modular tasks oriented in adjacent perpendicular planes. In this planar orientation, tasks will require very high skill levels for both symmetric and asymmetric motions. On the shown illustration, the user is required to describe a circle on a clockwise motion with one extremity on one plane wherein the other extremity is required to describe a counterclockwise circular motion on another plane that is perpendicular to the former.

FIG. 4a: Illustration of a mechanical unit in a rectangular solid wherein all three planar arrangements are shown as in FIG. 3a-3c. Symmetric tasks of FIGS. 2c and 2d on a single plane illustrates the planar orientation of FIG. 3a. Symmetric tasks of FIG. 2d on parallel opposing planes at both ends illustrates the planar orientation of FIG. 3b. Symmetric tasks of FIGS. 2c and 2d on adjacent perpendicular planes ends illustrates the planar orientation of FIG. 3c.

FIG. 4b: Illustration of a mechanical unit configured in a cube where planar orientation of FIG. 3b illustrates the relationship of symmetric tasks of FIGS. 2c and 2d on parallel opposite ends. Planar orientation of FIG. 3c is illustrated with asymmetric task in combination with FIGS. 2b, and 2d on one adjacent perpendicular plane or 2c on the other adjacent perpendicular plane.

FIG. 4c: Illustration of a mechanical unit configured in pyramid where an oblique planar orientation is illustrated with symmetric motions of FIG. 2c on two opposing planes. Pyramidal adjacent planar orientation is illustrated with combination of asymmetric motions of FIGS. 2b and 2c.

FIG. 4d: Illustration of a mechanical unit configured in truncated pyramid where the relationship of symmetric motions of FIGS. 2a and 2b is illustrated on opposing oblique planes.

FIG. 4e: Illustration of a mechanical unit configured in sphere where planar orientation of FIGS. 3b and 3c are illustrated with tasks on both ends of x, y and z axes so that opposing tasks are on parallel planes, while adjacent tasks are on perpendicular planes. All six tasks are interchangeable; the user installs any combination of available tasks.

FIG. 4f: Illustration of a mechanical unit configured in cylindrical solid shape where planar orientation of FIG. 3b is illustrated with symmetric motions of FIGS. 2c and 2d on parallel opposing planes. The user may install any combination of available tasks.

FIG. 5a: Illustration of an interactive activity unit with touch-sensitive remote devices utilizing Bluetooth technology to perform selected tasks that are tracked and displayed on digital screen. The digital display may be television, digital monitor, tablet or similar device. Input devices may be game controllers, joysticks, smartphones or motion-sensing devices utilizing Bluetooth technology to show the motion on the digital display. On the shown illustration, the user is defining an upward-downward motion on the touch-sensitive pad on the right activity area and a circular motion on the left.

FIG. 5b: Illustration of an interactive activity unit utilizing handheld motion-sensing Bluetooth devices to perform selected tasks that are tracked and displayed on a digital screen. The motion of each hand will be displayed on a screen reflecting the motions of the handheld units. Such motion-sensing devices are either handheld or wearable and utilize Bluetooth technology for continuously transmitting its position, and hence displaying the described motion.

FIG. 6a: Illustration of two extremity involvement where index fingers are shown executing tasks on a mechanical activity unit representing tasks being performed on parallel opposing planes.

FIG. 6b: Illustration of two extremity involvement in which both hands are involved in a bilateral brain-coordination activity as illustrated in FIG. 5b above using handheld motion-sensing devices.

FIG. 6c: Illustration of four extremity involvement where all hands and feet are involved in bilateral brain-coordination tasks on a rideable activity unit. These motions can be symmetric or asymmetric, and each can be set independently to operate in similar or opposing directions of rotation for the hands and for the feet, respectively.

This rideable mechanical activity unit might employ pre-assigned tasks or interchangeable modular tasks with or without electronic tracking for digital display.

FIG. 7: Illustration of mechanical activity unit utilizing electronic feedback. On the illustrated example, the user is required to slide a button on each side through the indicated path that combines symmetric and asymmetric motions on a single plane. The indicated path utilizes electrically conductive contact strips to track the correct motion through the track and button. Deviation from the correct path displays the "Fail" light. Successful completion results in displaying the "Pass" light.

SPECIFICATIONS: DESCRIPTION OF THE INVENTION

The current invention introduces a system of activities to be performed by multiple extremities for enhancing bilateral coordination of brain hemispheres via the use of mechanical, digital, electrical devices or a combination thereof, hereinafter, referred to as 'activity unit'. On each activity unit, the user is required to simultaneously perform a set of tasks, wherein each task is assigned to an extremity. The complexity of the said activity depends on the chosen combination of tasks, whether symmetric, opposing or asymmetric, and whether performed on a single plane or on multiple planes.

If the set of tasks are performed on multiple planes then the planar orientation can be parallel, perpendicular or oblique to each other.

The mechanical activity units are categorized in two types-(i) those that have preassigned set of tasks, and (ii) those that have options for the user to choose the set of tasks through interchangeable modular task units. Both types of these activity units vary based on size, shape, age, level of challenge, the types of provided tasks and the number of extremities needed to be involved. They are available as choice of handheld, tabletop, rideable and wearable units with or without an electronic and/or interactive interface.

The digital activity units utilize application-based tasks or modules and are categorized into two types of methods-(i) those that can be performed on touchscreen devices, and (ii) those that can be performed with the use of motion sensitive devices utilizing Bluetooth technology to monitor the corresponding motions on digital displays. Touchscreen-based tasks are performed on a single plane. Other tasks that are performed on multiple planes via multiple extremities utilize motion detection or motion-sensitive devices, e.g. wristband, remote controls, joysticks or other electro-mechanical units that senses and tracks the motions and display accordingly.

The difficulty level and the intensity of left and right brain coordination depend on the number of extremities being involved, the chosen combination of tasks and their planes of motion. Some examples of difficulty levels of activities can be illustrated by the following examples, please refer to the supplied diagrams and their corresponding descriptions.

Choose modular task FIG. 2c and FIG. 2d and attach them side-by-side to a single plane on the rectangular solid activity unit as shown in FIG. 4a. The required action for both index fingers involves rotating each button simultaneously in opposite directions, one clockwise and the other counterclockwise. This is an entry-level challenge.

Choose modular task FIG. 2c and FIG. 2d and attach them to opposite ends of the cylindrical activity unit in parallel planes as shown in FIG. 4f. Requiring simultaneous movement of both buttons either toward the user or away from the user requires entry-level skill.

Choose two of modular task of clockwise circular motion as shown in FIG. 2d and attach them to opposite ends of the activity unit as shown in FIG. 4a, and FIG. 4e. however requires simultaneous movement of buttons in opposing directions. While one is being rotated away from the user, the other toward the user in a circular motion now significantly increases the required skill to a moderate level.

Choose modular task FIG. 2b and FIG. 2d and attach them on adjacent surfaces of the cube activity unit in perpendicular planes as shown in FIG. 4b executes asymmetric motions and imposes higher difficulty. However, replacing modular task FIG. 2b with FIG. 2g makes executing the activity extremely difficult.

Choosing the rideable activity unit represented in FIG. 6c and using modular tasks FIG. 2c and FIG. 2d for left and right feet as shown while using modular tasks FIG. 2d and FIG. 2c for left and right hand requires intense bilateral brain coordination.

Although some activities are initially challenging, they usually become easier to perform with more practice as our brain coordination skills develop. Although outcomes resulting from use of this invention are yet to be tested and/or proven, it is expected that this increase in performance should reflect positive changes on motor skill and brain coordination ability in daily life. It is the opinion of the inventor that the system provides a natural progression in task difficulty, and that repetitive practice will promote mastery of the tasks and enhancement of brain coordination that are not limited to using this system or motor skill only, but in other life situations including ability to utilize the brain in thinking, creativity, logical decision and others, as well.

The invention claimed is:

1. A method of operating an activity unit by a user, comprising:

providing or obtaining an activity unit being a three-dimensional physical object having an outer face, the activity unit comprising:

a first activity module located on a first location of the outer face, the first activity module including a first physical object movable by direct contact manipulation by a first extremity of a user in a first direction of movement along a first predefined path on a first plane in a first task a second activity module located on a second, different location on the outer face and including a second physical object movable by direct contact manipulation by a second extremity of the user in a second direction of movement along a second predefined path on a second plane in a second task, and a first receptacle and a second receptacle on the first location of outer face and the second location of the outer face, respectively, the first receptacle and the second receptacle configured to accommodate the first activity module and the second activity module, respectively;

wherein the first plane does not coincide with the second plane; and a user simultaneously performing the first task and the second task by moving the first physical object by a first extremity of the user in a first direction of movement while moving the second physical object by a second extremity of the user in a second direction of movement, wherein the first direction and the second direction are different; and the user removing at least one of the first activity module and the second activity module from the activity unit, and replacing the removed at least one of the first activity module and the second activity module by a third activity module by placing the third activity being onto one of the first receptacle and the second receptacle from which the at least one of the first activity module and the second activity module has been removed.

2. The method of claim 1, wherein the first plane and the second plane are parallel, perpendicular, or angular to each other.

3. The method of claim 1, wherein the first direction of movement and the second direction of movement are asymmetrical.

4. The method of claim 1, wherein the first direction of movement and the second direction of movement are symmetrical.

5. The method of claim 1, wherein the first direction of movement follows one of a straight, curved, or irregular path.

6. The method of claim 1, wherein the first task comprises repetitive, sequential, or alternating movements.

7. The method of claim 1, wherein the activity unit is at least one of a handheld unit, a stationary unit, and a rideable unit.

8. The method of claim 1, wherein the activity unit is one of a spherical, cylindrical, cubic, cuboid, prism, or complex shape.

9. The method of claim 1, wherein the first extremity is one of a hand, a foot, or a finger.

* * * * *